United States Patent [19]
Tomlinson et al.

[11] Patent Number: 4,622,053
[45] Date of Patent: Nov. 11, 1986

[54] SEPARATION OF HYDROCARBON MIXTURES

[75] Inventors: Terence R. Tomlinson, Stockport, United Kingdom; Donald R. Cummings, Burradoo Nr. Bowral, Australia

[73] Assignee: Petrocarbon Developments Limited, Manchester, United Kingdom

[21] Appl. No.: 650,724

[22] Filed: Sep. 14, 1984

Related U.S. Application Data

[63] Continuation-in-part of Ser. No. 553,640, Nov. 21, 1983, abandoned.

[30] Foreign Application Priority Data

Sep. 20, 1983 [GB] United Kingdom ................. 8325069
Jul. 31, 1984 [GB] United Kingdom ................. 8419488

[51] Int. Cl.$^4$ ............................................... F25J 3/02
[52] U.S. Cl. ........................................ 62/26; 62/30; 62/31; 62/34; 62/39
[58] Field of Search ................................. 62/23-31, 62/34, 38, 39

[56] References Cited

U.S. PATENT DOCUMENTS 4,266,958 5/1981 Cummings .............................. 62/17
4,519,825 0/0000 Bernard et al. .

FOREIGN PATENT DOCUMENTS 1257372 of 0000 United Kingdom .
1571073 of 0000 United Kingdom .
2110808 of 0000 United Kingdom .

Primary Examiner—Frank Sever
Attorney, Agent, or Firm—Browdy and Neimark

[57] ABSTRACT

In the process for the recovery of e.g. LPG or NGL and sales gas from a gaseous hydrocarbon feed 11 by partially condensing the feed in heat exchanger 1 at superatmospheric pressure, separating the condensate from the uncondensed gas in gas/liquid separator 2, rectifying the uncondensed gas to produce the sales gas and stripping the condensate to produce the LPG or NGL, substantially power savings are obtained if the rectification is effected in a reflux exchanger 103 and the stripping is effected in a separate distillation column 203.

16 Claims, 5 Drawing Figures

SEPARATION OF HYDROCARBON MIXTURES

This application is a continuation-in-part application of U.S. Ser. No. 553,640, filed Nov. 21, 1983, now abandoned.

This invention relates to the separation of multi-component hydrocarbon mixtures and in particular to the separation of $C_3$ and higher hydrocarbon from gas mixtures which also contain methane and/or hydrogen. The invention is particularly applicable to the recovery of natural gas liquids (NGL) and liquefied petroleum gas (LPG) from naturally occurring or synthetic hydrocarbon streams.

According to one method for the recovery of NGL or LPG from gas containing also lighter components such as hydrogen and/or methane, the feed gas is cooled at superatomspheric pressure to partially condense it, and the NGL or LPG, as appropriate, is obtained from the condensate by stabilising the condensate by stripping in a distillation column or similar device. The uncondensed light gas is expanded through a turbine to provide the refrigeration for the process, thereby undergoing partial liquefaction, and then supplied to the top of the column for rectification. The rectified gas, which will be largely methane and/or hydrogen, is suitable for disposal as a sales gas.

While this method has gained wide acceptance in practice, there is a need for a more efficient alternative where the sales gas is required at a pressure close to that of the feed gas, especially where this sales gas forms a major proportion of the feed. This is because to obtain high recovery of the LPG or NGL, the distillation column has to operate at a relatively low pressure, with a correspondingly low top temperature, with the consequence that the power recovery from the expander is also low and substantial energy has to be expended in recompressing the light gas.

It has now been found that the power requirement can be substantially reduced by rectifying the uncondensed gas in a refluxing exchanger because this enables the required refrigeration for the rectification to be provided over the whole temperature range of the rectification rather than just at the cold end where the energy requirement for providing the refrigeration will be highest.

A further advantage is that any expansion of uncondensed light gas to provide refrigeration for the process can now be effected after rectification. This not only reduces the loss of heavy components into the light gas but permits the rectification to take place at a higher pressure than in the conventional process. Further, any liquid formed in the expander does not have to supply reflux to a distillation column. Even allowing for the recompression of the expanded gas to feed gas pressure, the overall power requirement is substantially less than that previously required.

A consequential benefit of being able to effect the rectification at a higher pressure is that it is now possible to carry out the final stripping of the liquid product at a higher temperature which can even be at or above ambient temperature thereby minimising the consumption of utilities.

Still further benefits in power saving can be achieved by providing at least a part of the refrigeration from an external source since this will reduce or eliminate the need for expansion of the light gas and the power required for the external refrigeration is more than offset by the reduction or elimination of the work of recompressing the expanded light gas.

Thus, according to the present invention, there is provided a process for the separation of a light gas which contains methane and/or hydrogen, and which forms a major part (by volume) of the feed gas mixture, from a heavier stream containing $C_3$ hydrocarbon optionally together with $C_2$ hydrocarbon and/or hydrocarbon containing 4 or more carbon atoms, the method comprising (i) cooling the feed gas mixture at superatmospheric pressure to partially condense it,
(ii) separating the condensate from the uncondensed gas,
(iii) rectifying the uncondensed gas to produce said light gas, and,
(iv) stripping the condensate to produce said heavier portion, wherein said rectification of step (iii) is effected by further cooling the uncondensed gas to partially condense it while passing it upwards whereby the liquid condensed out of said gas flows downwards in countercurrent fashion in contact with the rising gas and forms a mixture with condensate formed by the partial condensation, and step (iv) involves stripping said mixture in a distillation column to produce said heavier portion.

Cold for the process may be provided from a process stream, e.g. by expansion of the rectified gas, and/or by means of external refrigeration (by which we mean refrigeration which does not involve the use of a process stream).

In one embodiment which employs expansion of the rectified gas to provide cold for the process, the rectified gas recovered from the top of the refluxing exchanger is passed back to provide refrigeration at the warm end of that exchanger and then work expanded and employed to provide refrigeration at the cold end of the exchanger. In another embodiment, the rectified gas may be work expanded and then passed back through the refluxing exchanger to provide in one pass refrigeration for both the cold and warm ends and external refrigeration is employed to assist in cooling the feed gas mixture in step (i). In both cases the expanded rectified gas recovered from the refluxing exchanger may then be used in cooling the feed gas mixture in step (i).

A particularly suitable way of providing all the refrigeration by external refrigeration is by means of a multi-stage vapour compression cascade refrigerator. However, alternative sources of cold may be used if desired. Multi-stage vapour compression cascade refrigerators are known per se and comprise a system of two or more interrelated, and generally closed, refrigeration loops so arranged that the condensation of a primary refrigerant is effected by indirect heat exchange with evaporating secondary refrigerant and, if there are more than two loops, the condensation of the secondary refrigerant is effected by indirect heat exchange with evaporating tertiary refrigerant, and so on, whereby cold is produced at progressively lower temperatures in the loops, the primary refrigerant being in the coldest loop. A preferred embodiment employs a two-stage vapour compression cascade refrigerator, with refrigeration for the refluxing exchanger being provided by evaporating primary refrigerant while evaporation of a part of the secondary refrigerant is employed in cooling the feed gas mixture.

In the process of the present invention, the cooling of the feed gas mixture to partially condense it may be effected in one or more steps. Where more than one step is employed, e.g. to separate hydrocarbons boiling above a desired maximum temperature, the condensate will usually be separated after each step and the uncondensed gas will be subjected to one or more further cooling steps with separation of the condensate formed in each step.

Depending on the composition desired in the light gas and the heavier portion, any $C_2$ hydrocarbons in the feed gas may be retained in the uncondensed portion or in the condensate, as desired, and subsequently may be separated from the uncondensed portion or the condensate, or not, as desired.

The process of the invention is particularly applicable for the separation of NGL or LPG from natural gas or from other hydrocarbon streams containing them, e.g. refinery streams and by-product streams of chemical processes, especially where the light gas which is recovered by the process forms 90% or more, by volume, of the feed gas stream.

Where external refrigeration is employed, expansion of the uncondensed gas can be avoided and this gas can therefore be recovered close to the feed gas pressudre after rectification, without recompression. Since the process of the invention permits the stripping step to be effected at or above ambient temperature, the reboil therefor may be provided by low grade heat and need not be a significant cost item. The gas recovered in the stripping step may suitably be combined with the feed to the process for recycle.

While the feed gas may be supplied at any suitable pressure, design considerations will generally dictate a preferred maximum of about 50 bar absolute. In general, it will be preferred that the feed gas is supplied at a pressure of at least about 20 bar. However, higher or lower pressures may also be employed.

The invention will now be described with reference to preferred embodiments and with the aid of the accompanying drawings in which FIG. 1 is a flow diagram of a conventional plant for the separation of NGL or LPG from lighter gases and wherein the cold for the process is provided by expansion of the light gas;

Figure 4:
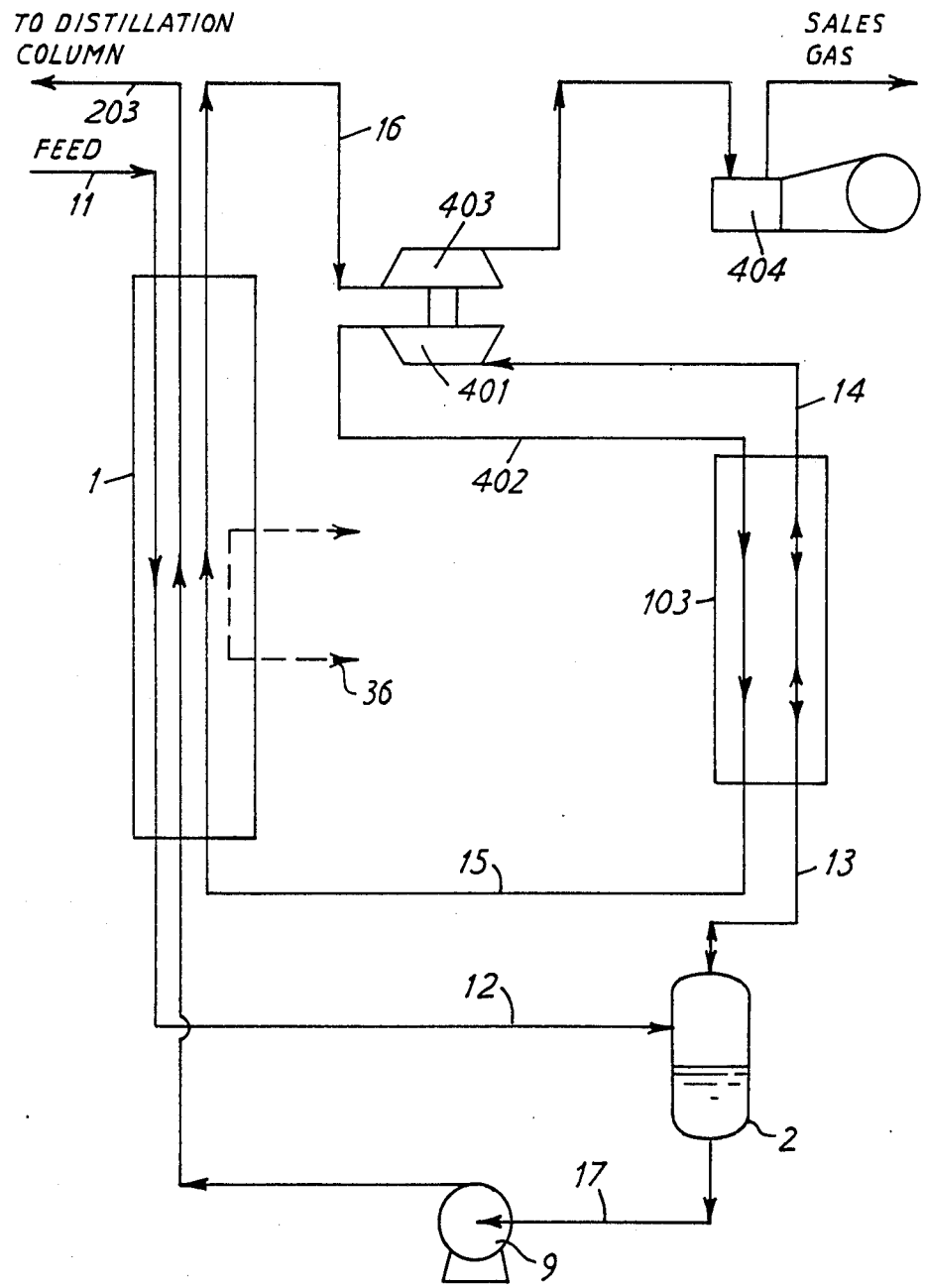
Figure 5:
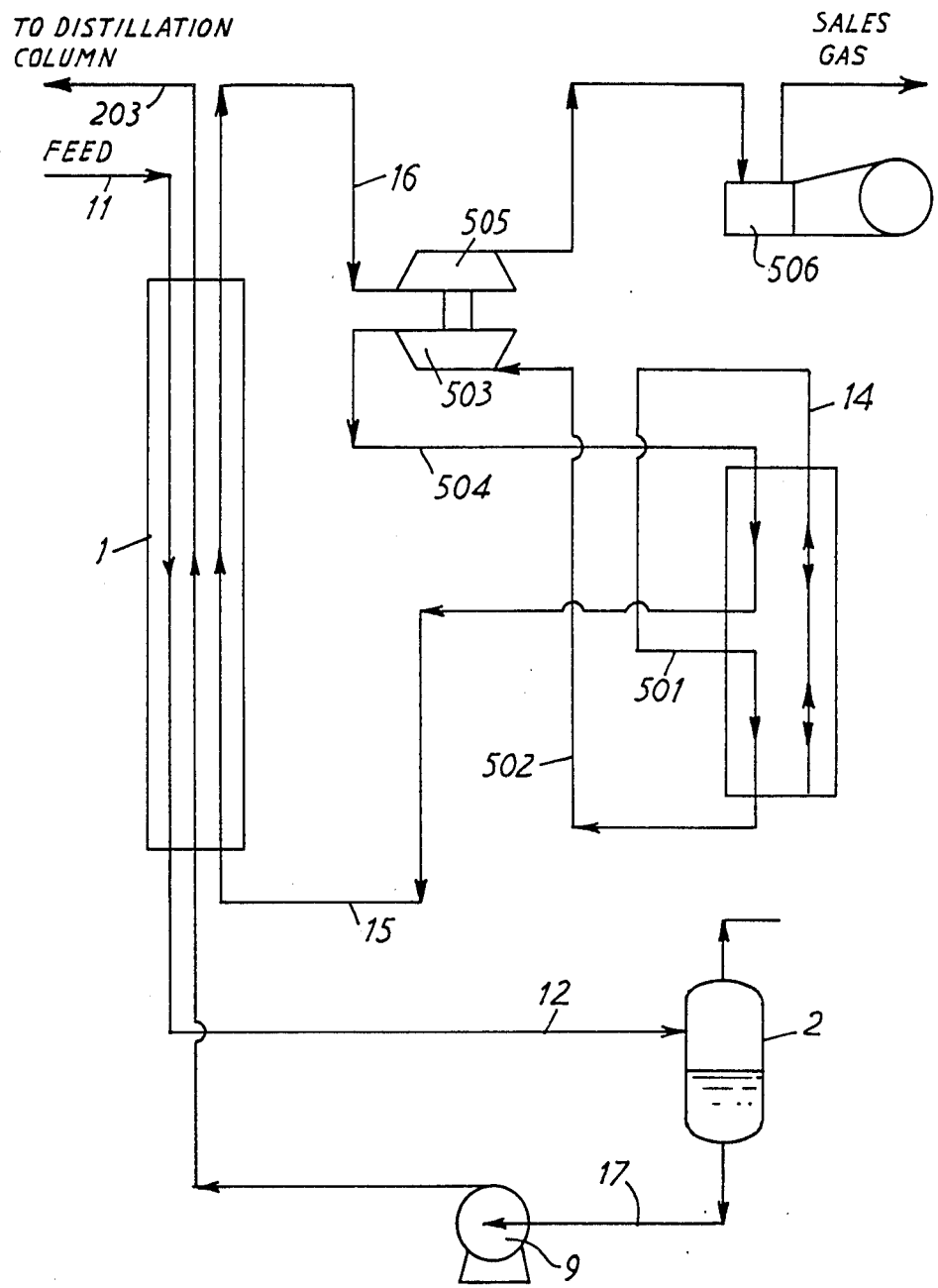

FIG. 4 is a flow diagram of a part of a process in accordance with a second embodiment of the invention which employs in part external refrigeration and in part refrigeration provided by work expansion of the uncondensed gas; and FIG. 5 is a flow diagram of a part of a process in accordance with a third embodiment of the invention wherein the refrigeration is provided by work expansion of the uncondensed gas.

Figure 1:
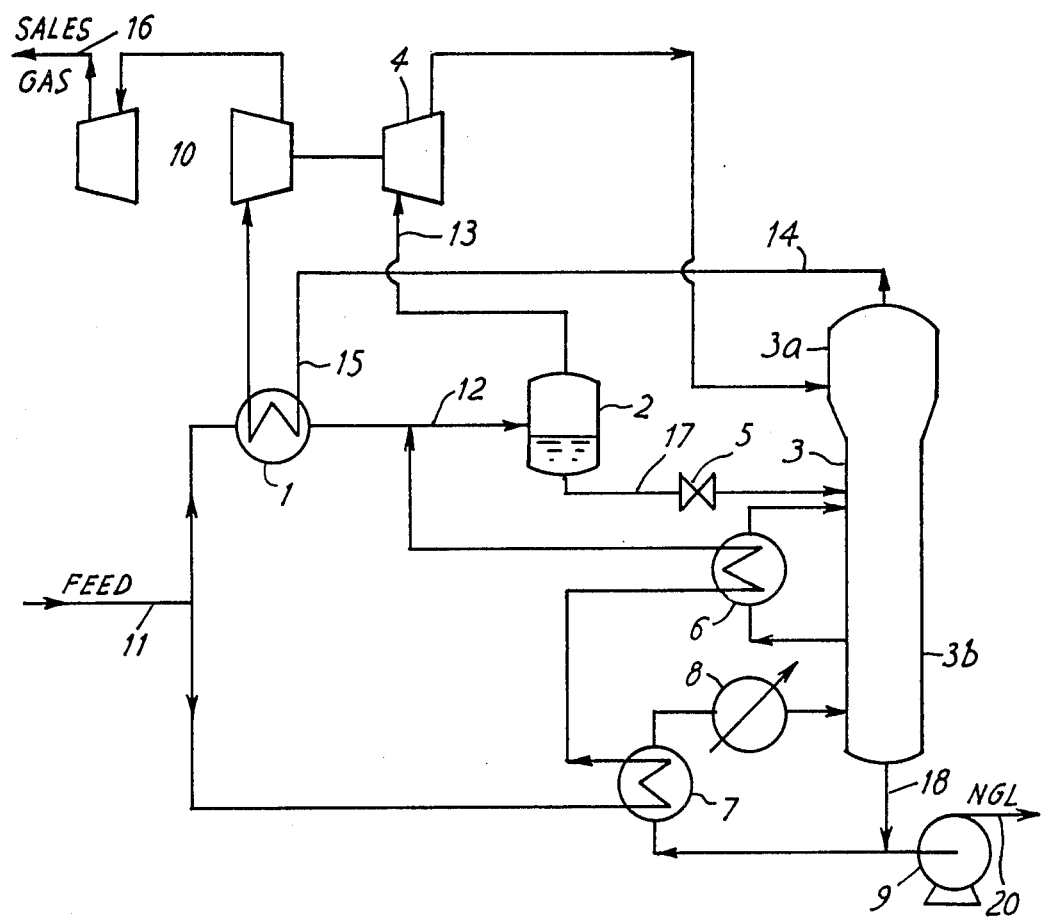

In FIG. 1, 1 is a main heat exchanger for partially condensing the feed gas mixture, 2 is a gas/liquid separator, 3 is a distillation column having a rectification section 3a and a stripping section 3b, 4 is an expansion turbine, 5 is an expansion valve, 6 and 7 are secondary heat exchangers, 8 is a reboiler for the distillation column, 9 is a pump for NGL product and 10 is a two-stage compressor. Feed gas mixture is supplied to the plant in line 11 e.g. at 40 bar pressure, and generally at about ambient temperature. A first part of this feed is cooled and partially condensed in heat exchanger 1 and then passed via line 12 to gas/liquid separator 2 where the uncondensed gas is separated from the condensate. The uncondensed gas in line 13 is expanded through expansion turbine 4 to cause partial liquefaction and the partially liquefied gas is then fed to rectifying section 3a of the column 3. The rectified gas recovered from the top of the column in line 14 is passed back via line 15 to heat exchanger 1 where it passes in indirect counter-current heat exchange with the feed gas mixture in line 11 to cool and partially condense it. The gas is thereafter recompressed to the desired delivery pressure in compressor 10 and recovered through line 16 as sales gas.

The liquid formed by the partial condensation is recovered from gas/liquid separator 2 in line 17, expanded in valve 5 to column pressure and fed to the stripping section 3b of the column 3. The desired product, e.g. NGL, is recovered from the column bottom in line 18. A part of this product is re-vaporised in heat exchanger 7 and reboiler 8 and returned to the column as reboil, the remainder is pumped to line 20 for recovery as NGL product. The heat medium for heat exchanger 7 and also for side reboiler 6, where this is used, is provided from a second part of the feed gas mixture which is thereafter passed to join the first part of the feed gas mixture downstream of heat exchanger 1 in line 12.

By way of example of the process described with reference to FIG. 1, a feed gas having the composition and flow rate indicated in Table 1 below, and supplied at a pressure of 40 bar absolute and at a temperature of 301° K., was separated to produce an NGL stream and a Sales Gas stream each having the composition and flow rate indicated in the table below and each delivered at a pressure close to the feed gas supply pressure of 40 bar absolute. The power requirement of the process was 1800 BHP.

TABLE 1

|  | Feed Gas | NGL | Sales Gas |
|---|---|---|---|
| Composition (Volume %) |  |  |  |
| $C_1$ | 90.3 | — | 93.7 |
| $C_2$ | 6.4 | 15 | 6.1 |
| $C_{3+}$ | 3.3 | 85 | 0.2 |
| Flow Rate (m³/hr) | 27940 | 1020 | 26920 |

Figure 2:
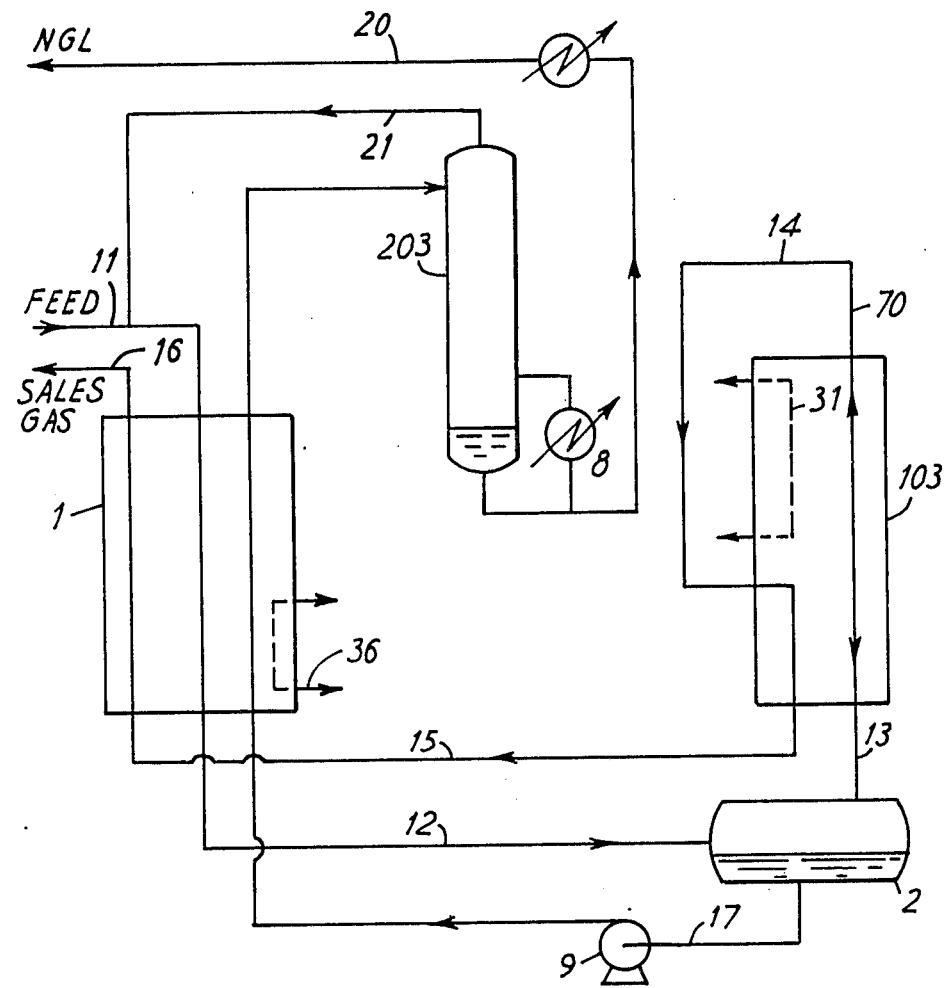
FIG. 2 is a flow diagram of a process according to one embodiment of the present invention in which all the refrigeration is provided by external refrigeration.
Figure 3:
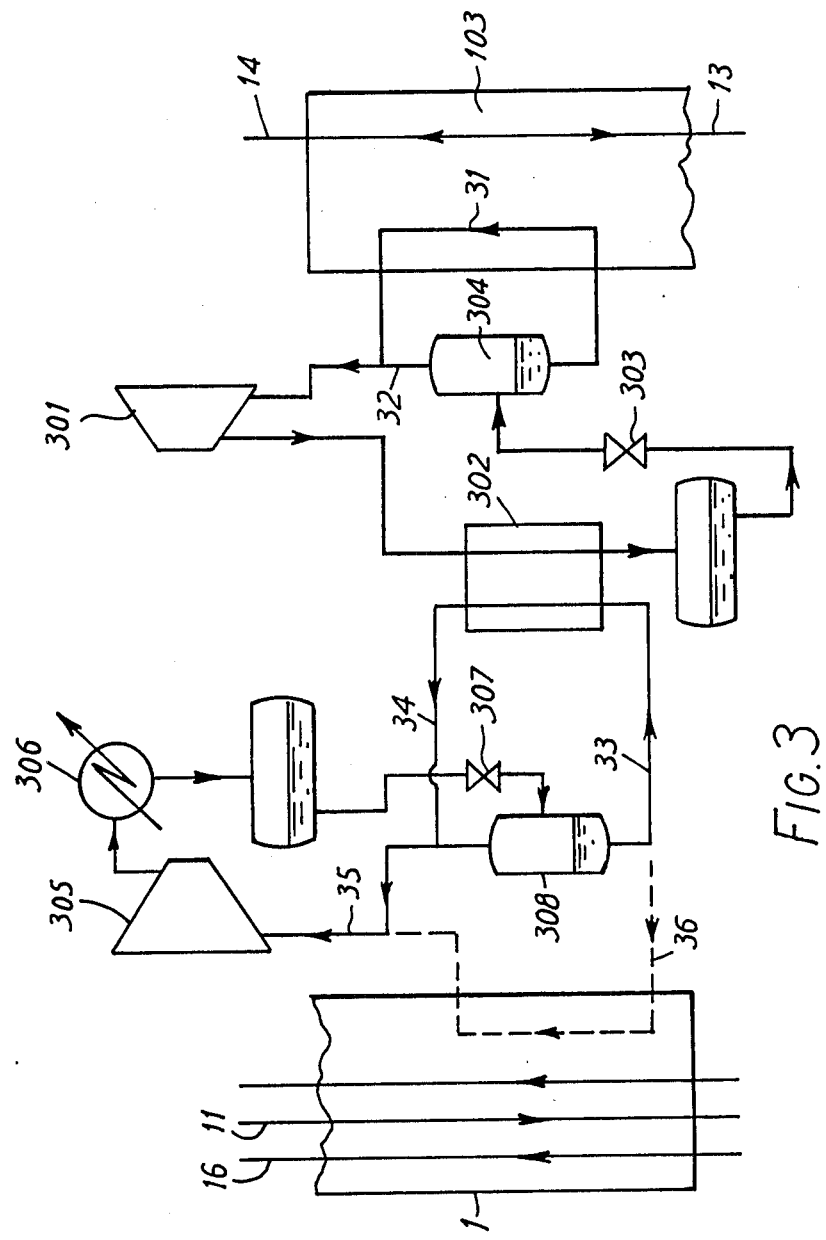
FIG. 3 is a flow diagram of a two-stage vapour compression cascade refrigerator system suitable for use in the arrangement of FIG. 2.

In FIGS. 2 and 3, which illustrate a process incorporating the present invention, the apparatus and process lines which are common to the arrangement illustrated in FIG. 1 are identified by the same reference numerals. In this arrangement, however, the distillation column 3 is replaced by a refluxing exchanger 103 and a stripper 203 and the expansion turbine 4 and two-stage compressor 10 are omitted.

In the process illustrated in FIGS. 2 and 3 a feed gas having the same composition as that described above and at the same pressure of about 40 bar is admitted to heat exchanger 1 through line 11 at about ambient temperature and cooled to about −40° C. with returning product streams the nature of which are described more fully below. Leaving through line 12 as a two phase mixture, the feed is separated in gas/liquid separator 2 and the uncondensed gas in line 13 passed upwards in passages of refluxing exchanger 103 where it is further cooled by refrigerant passing through line 31 and the nature of which is described in more detail below with reference to FIG. 3. The condensate formed by this further cooling descends in line 13 in direct counter-current with and in intimate contact with the rising gas and returns to the gas/liquid separator 2 where it mixes with the condensate therein.

The gas recovered from the top of refluxing exchanger 103 in line 14 contains very little propane and virtually no heavier hydrocarbons and is typically at a tempeature of about −70° C. This gas is passed back through further passages of the heat exchanger at the warm end thereof in line 15 and thence back through heat exchanger 1 from which it is withdrawn as sales gas through line 16 at substantially the same pressure as that at which the feed gas mixture is supplied.

The liquid in separator 2, containing condensate formed in the refluxing exchanger 103, is recovered through line 17 and pumped back through exchanger 1 by pump 9. Leaving the exchanger at near-ambient temperature, it is fed to the top of stripper column 203 and the gas stripped from the liquid therein is recovered in line 21, typically at about 35° C., and returned to feed line 11. The stripped liquid is recovered from the bottom of the column in line 18, typically at about 95° C. A first part is returned through reboiler 8 to the bottom of the column and the remainder is recovered through line 20 as NGL product. Reboiler 8, which typically reheats the bottoms product to about 90°-120° C., is suitably heated with hot oil or low pressure steam.

The refrigerant in line 31 comprises evaporating working medium in the primary loop of a two-stage vapour compression cascade refrigerator as illustrated in FIG. 3. In the first, or primary, stage of the refrigerator, primary refrigerant is compressed in compressor 301, the compressed refrigerant is cooled and condensed in heat exchanger 302, expanded through expansion valve 303 and passed to gas/liquid separator 304. Any gas remaining uncondensed is recovered through line 32 and returned to compressor 301 for recompression and recycle. The condensate is transferred from the gas/liquid separator 304 to line 31 where it is evaporated in indirect heat exchange with the process stream in line 13 in refluxing exchanger 103 (see FIG. 2). The evaporated medium is thereafter passed to line 32 for return, with any uncondensed gas from gas/liquid separator 304, to compressor 301.

The condensation of the primary refrigerant medium in heat exchanger 302 is effected by indirect heat exchange with evaporating secondary medium in line 33. This secondary medium is then returned via lines 34 and 35 to compressor 305 where it is recompressed, cooled in heat exchanger 306 and condensed, expanded through expansion valve 307 and passed to gas/liquid separator 308 from which the condensate is recovered and passed to line 33 for evaporation in heat exchanger 302 as previously described.

If additional refrigeration is required in heat exchanger 1 (see FIG. 2) this may conveniently be provided by diverting a part of the condensate formed in gas/liquid separator 308 to line 36 (shown as a broken line in FIG. 3) for evaporation in heat exchanger 1 in indirect heat exchange relationship with the feed gas mixture in line 11. The evaporated medium is then returned to join line 35 for recompression in compressor 305 and recycle.

In the two-stage cascade refrigerator described in FIG. 3 and operating at the temperatures described, the primary refrigerant may suitably be ethane or ethylene, for example, and the secondary refrigerant propane. However other refrigerants having suitable bubble and dew points may be employed, including mixed refrigerants.

By way of example, a process as described above with reference to FIGS. 2 and 3, and operated to produce NGL and Sales Gas having the same flow rates and compositions as described in Table 1, and at a pressure of about 40 bar absolute, from the feed gas mixture described in Table 1 and provided at the same pressure and temperature and at the same rate of flow as described above with reference to FIG. 1, had a total power requirement of only 700 BHP, showing a remarkable 61% saving in power as compared with the process described in FIG. 1.

The refrigeration was provided using ethylene in the primary (i.e. low) temperature loop of the cascade refrigerator at a flow rate of 2390 m$^3$/hr with the high pressure side at 20 bar absolute and the low pressure side at 4.4 bar absolute, and propane in the secondary loop at a flow rate of 4130 m$^3$/hr with the high pressure side at 17.5 bar absolute and the low pressure side at 1.4 bar absolute. About 33% of the propane was passed through line 36 to provide additional refrigeration for the heat exchanger 1.

The relevant temperatures in the plant were as follows:

| LINE | T (°K.) |
| --- | --- |
| 11 | 305 |
| 12,13,17 | 233 |
| 14 | 203 |
| 15 | 228 |
| 18 | 368 |
| 21 | 308 |

The two-stage cascade refrigerator employed in the process described in FIG. 2 may be replaced by some other form of external refrigeration, if desired. For example a single loop vapour compression refrigerator employing a mixed refrigerant may be employed but the power saving wil not be so great.

While one objective of the process is to avoid expansion of the light gas, the possiblity of some expansion of one or more of the process streams, namely feed gas, condensate before or after stripping and uncondensed gas before or after rectification, is not excluded. Where any such expansion is employed, any cold so produced may be employed in the process, if desired, e.g. to assist stripping, rectification and/or cooling the feed gas. The flow diagram for a part of one such process is illustrated in FIG. 4 wherein the apparatus and process lines which are common to the arrangement illustrated in FIGS. 2 and 3 are identified by the same reference numerals. The operation of this arrangement is the same as that of FIGS. 2 and 3 except that in this arrangement, the uncondensed gas recovered in line 14 from the refluxing exchanger 103 is expanded in turbine expander 401 and the expanded gas is passed in line 402 back through the entire length of the refluxing exchanger to provide the refrigeration therefor, thereby omitting the need for external refrigeration loop 31. After subsequent passage through main heat exchanger 1 to cool the feed gas mixture in line 11 by indirect counter-current heat exchange, the gas recovered in line 16 is partially recompressed in compressor 403 which is driven by expander 401 and finally restored to about feed gas pressure by supplementary compressor 404. As in the arrangement of FIGS. 2 and 3, pump 9 pumps the liquid in line 17 back through heat exchanger 1 and thence to distillation column 203, not shown, for stripping.

By way of example, a process as described with reference to FIG. 4 and operated to produce NGL and Sales Gas having the same flow rates and compositions as described in Table 1, and at the same delivery pressures, from the feed gas mixture described in Table 1 and provided at the same temperature and pressure and at the same flow rate as described above with reference to FIG. 1 required 230 BHP refrigeration compression to supply that part of the required refrigeration provided by evaporating propane through line 36, and 920 BHP for recompressing the gas in compressors 403 (at 70% efficiency) and 404 of which 150 BHP was provided by turbine expander 401, at an expander efficiency of 78%, making a net total power requirement of 1000 BHP.

While this is not as efficient as the arrangement of FIGS. 2 and 3, it still exhibits a saving of 45% as compared with the prior art arrangement of FIG. 1.

The relevant temperatures and pressures in the plant were as follows:

| LINE | T (°K.) | P (bar absolute) |
|---|---|---|
| 11 | 305 | 40 |
| 12,13,17 | 233 | |
| 14 | 203 | |
| 402 | 186 | 22 |
| 15 | 226 | |

The temperatures of the overhead and bottom streams from distillation column 203 were the same as for the process described above with reference to FIGS. 2 and 3.

FIG. 5 is a flow diagram of part of an arrangement for a process according to the invention wherein all the refrigeration is provided by expansion of the uncondensed gas. The apparatus and process lines which are common to the arrangement in FIGS. 2 and 3 are identified by the same reference numerals. The operation of this arrangement is the same as that of FIGS. 2 and 3 except that in this arrangement, the uncondensed gas recovered in line 14 from refluxing exchanger 103 is first passed back in line 501 as a refrigerant stream for the warm end of the said exchanger, and then is passed via line 502 to turbine expander 503 where it is work expanded and cooled and the expanded gas is then passed in line 504 as refrigerant for the cold end of exchanger 103. Thereafter, it passes back through main heat exchanger 1 to cool the feed gas mixture in line 11 by indirect counter-current heat exchange, is partially recompressed in compressor 505 which is driven by expander 503 and finally restored to close to feed gas pressure by supplementary compressor 506. As in the arrangement of FIGS. 2 and 3, pump 9 pumps the liquid in line 17 back through heat exchanger 1 and thence to distillation column 203, not shown, for stripping.

By way of example, in a process as described with reference to FIG. 5, and operated to produce NGL and Sales Gas having the same flow rates and compositions as described in Table 1 and at the same delivery pressures, from the feed gas mixture described in Table 1 and provided at the same temperature and pressure and at the same flow rate as described above with reference to FIG. 1, the power requirement of compressors 505 (at 70% efficiency) and 506 was 1630 BHP of which 330 BHP was supplied by the turbine expander 503 at 78% efficiency leaving a net power consumption of 1300 BHP. While this is less efficient than the arrangement of FIG. 4, it still exhibits a saving of about 28% as compared with the prior art arrangement of FIG. 1.

The relevant temperatures and pressures in the plant were as follows:

| LINE | T (°K.) | P (bar absolute) |
|---|---|---|
| 11 | 305 | 40 |
| 12,13,17 | 233 | |
| 14 | 203 | |
| 502 | 228 | |
| 504 | 184 | 14 |
| 15 | 203 | |

The temperatures of the overhead and bottom streams from distillation column 203 were the same as for the process described above with reference to FIGS. 2 and 3.

We claim:

1. In a process for the separation of a light gas which contains methane and/or hydrogen, and which forms a major part (by volume) of the feed gas mixture, from a heavier stream containing $C_3$ hydrocarbon, optionally together with $C_2$ hydrocarbon and/or hydrocarbon containing 4 or more carbon atoms, which process comprises:

(i) cooling the feed gas mixture at superatmospheric pressure to partially condense it, (ii) separating the condensate from the uncondensed gas, (iii) rectifying the uncondensed gas to produce said light gas, and (iv) stripping the condensate to produce said heaver portion, the improvement by which the light gas is obtained at a pressure close to that of the feed gas, comprising:

effecting said rectification of said uncondensed gas in step (iii) by passing uncondensed gas upwards, at substantially the same pressure as that at which it is obtained from step (ii), while further cooling the uncondensed gas to partially condense it, whereby the liquid condensed out of said gas flows downwards in counter-current fashion in contact with the rising gas and forms a mixture with condensate formed by the partial condensation;

prior to said stripping step (iv), warming said condensate by indirect heat exchange with the feed gas mixture; and effecting said step (iv) by stripping of said condensate in a stripping column to produce said heavier portion.

2. A process as claimed in claim 1 wherein the cold for the process is provided by external refrigeration.

3. A process as claimed in claim 2 wherein the external refrigeration is provided by a multi-stage vapour compression cascade refrigerator.

4. A process as claimed in claim 3 wherein refrigeration for step (iii) is provided by evaporating primary refrigerant of a two-stage vapour compression cascade refrigerator and refrigeration for step (i) is provided by evaporating a portion of the secondary refrigerant of said refrigerator.

5. A process as claimed in claim 1 wherein the cold for the process is provided by expansion of rectified gas.

6. A process as claimed in claim 1 wherein the cold for the process is provided in part by expansion of rectified gas and in part by external refrigeration.

7. A process as claimed in claim 6 wherein the external refrigeration is provided by a multi-stage vapour compression cascade refrigerator.

8. A process as claimed in claim 6 wherein refrigeration for step (iii) is provided by expansion of rectified gas and refrigeration for step (i) is provided by external refrigeration.

9. A process as claimed in claim 1 wherein the feed gas mixture is supplied at a pressure of from about 20 to about 50 bar absolute.

10. A process as claimed in claim 1 wherein step (iv) is effected at a temperature at or above ambient temperature.

11. A process as claimed in claim 1 in which gas recovered from step (iv) is combined with the feed gas mixture for recycle.

12. A process as claimed in claim 1 for the production of natural gas liquid.

13. A process as claimed in claim 1 for the production of liquid petroleum gas.

14. A process as claimed in claim 1 wherein the light gas comprises at least 90% of the feed gas mixture.

15. Natural gas liquid or liquid petroleum gas when produced by the process claimed in claim 1.

16. A process in accordance with claim 1, wherein said rectification step (iii) takes place in a refluxing exchanger.

* * * * *